United States Patent
Arluck et al.

(10) Patent No.: US 9,604,889 B2
(45) Date of Patent: *Mar. 28, 2017

(54) ISOBARIC PRESSURE EXCHANGER IN AMINE GAS PROCESSING

(71) Applicant: Energy Recovery, Inc., San Leandro, CA (US)

(72) Inventors: James Lee Arluck, Hayward, CA (US); Jeremy Grant Martin, Oakland, CA (US); Prem Krish, Foster City, CA (US)

(73) Assignee: ENERGY RECOVERY, INC., San Leandro, CA (US)

(*) Notice: Subject to any disclaimer, the term of this patent is extended or adjusted under 35 U.S.C. 154(b) by 286 days.

This patent is subject to a terminal disclaimer.

(21) Appl. No.: 14/074,530

(22) Filed: Nov. 7, 2013

(65) Prior Publication Data

US 2014/0128655 A1    May 8, 2014

Related U.S. Application Data

(60) Provisional application No. 61/724,031, filed on Nov. 8, 2012.

(51) Int. Cl.
*C07C 7/11* (2006.01)
*B01D 53/18* (2006.01)
(Continued)

(52) U.S. Cl.
CPC ............ *C07C 7/11* (2013.01); *B01D 19/0005* (2013.01); *B01D 53/1456* (2013.01);
(Continued)

(58) Field of Classification Search
None
See application file for complete search history.

(56) References Cited

U.S. PATENT DOCUMENTS

| 4,138,230 A | 2/1979 | Thompson |
| 4,471,795 A | 9/1984 | Linhardt |

(Continued)

FOREIGN PATENT DOCUMENTS

| CN | 1694753 A | 11/2005 |
| CN | 101208145 A | 6/2008 |

(Continued)

OTHER PUBLICATIONS

A100 Amine Gas Treating System. Datasheet [online]. Exterran, Created: Dec. 8, 2012 [Retrieved on Feb. 15, 2014]. Retrieved from the Internet: <URL: http://www.exterran.com/Content/Docs/Products/A100-Amine-System-English-A4.pdf>, pp. 1-4.

(Continued)

*Primary Examiner* — Tam M Nguyen
(74) *Attorney, Agent, or Firm* — Fletcher Yoder, P.C.

(57) ABSTRACT

A system includes an amine gas processing system that includes a contactor configured to remove an acid gas from an untreated natural gas using an amine in a lean amine stream, output a treated natural gas, and output a rich amine stream. The system also includes a regenerator configured to regenerate the amine in the rich amine stream, output the lean amine stream, and output the acid gas. The system also includes an isobaric pressure exchanger (IPX) configured to transfer the rich amine stream from the contactor to the regenerator and to transfer the lean amine stream from the regenerator to the contactor.

13 Claims, 8 Drawing Sheets

(51) Int. Cl.
*B01D 19/00* (2006.01)
*B01D 53/14* (2006.01)
*C10L 3/10* (2006.01)
*F04F 13/00* (2009.01)

(52) U.S. Cl.
CPC .............. *B01D 53/18* (2013.01); *C10L 3/102* (2013.01); *F04F 13/00* (2013.01); *B01D 2256/245* (2013.01); *B01D 2257/304* (2013.01); *B01D 2257/504* (2013.01)

(56) References Cited

U.S. PATENT DOCUMENTS

| | | | |
|---|---|---|---|
| 4,798,910 | A | 1/1989 | Herrin |
| 6,071,484 | A | 6/2000 | Dingman et al. |
| 6,692,642 | B2 | 2/2004 | Josse |
| 7,066,257 | B2 | 6/2006 | Wellington et al. |
| 2003/0205378 | A1 | 11/2003 | Wellington et al. |
| 2009/0205496 | A1 | 8/2009 | Idem et al. |
| 2011/0044824 | A1* | 2/2011 | Kelada .................... F03G 7/005 417/53 |
| 2011/0100218 | A1 | 5/2011 | Wolfe |
| 2011/0283690 | A1 | 11/2011 | Bollinger et al. |

FOREIGN PATENT DOCUMENTS

| | | |
|---|---|---|
| CN | 202315685 U | 7/2012 |
| EP | 2481470 A1 | 8/2012 |
| FR | 2952710 | 5/2011 |
| WO | 2012024804 A1 | 3/2012 |

OTHER PUBLICATIONS

International Search Report and Written Opinion PCT/US13/69328 mailed on Mar. 18, 2014, pp. 1-9.
EP Extended Search Report; Application No. EP 13852928.4; Dated Jun. 1, 2016; 8 pages.
CA Office Action and Examination Search Report; Application No. CA 2,890,743; Dated May 25, 2016; 4 pages.
CN First Office Action and English Translation; Application No. CN 201380069730.0; Dated Apr. 19, 2016; 11 pages.
Unofficial English Translation of the second CN Office Action, dispatched Dec. 15, 2016, Application No. 201380069730.0, 11 pages.

* cited by examiner

ISOBARIC PRESSURE EXCHANGER IN AMINE GAS PROCESSING

CROSS-REFERENCE TO RELATED APPLICATION

This application claims priority to and benefit of U.S. Provisional Patent Application No. 61/724,031, entitled "ISOBARIC ENERGY RECOVERY DEVICE (ERD) IN AMINE GAS PROCESSING," filed on Nov. 8, 2012, which is hereby incorporated by reference in its entirety for all purposes.

This application relates to U.S. Provisional Patent Application No. 61/724,056, entitled "ISOBARIC ENERGY RECOVERY DEVICE (ERD) CONTROLS IN AMINE GAS PROCESSING," filed on Nov. 8, 2012, which is herein incorporated by reference in its entirety for all purposes.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The subject matter disclosed herein relates to natural gas processing, and, more particularly, to systems and methods for using an isobaric pressure exchanger (IPX) during natural gas processing using water-based amine solutions.

Natural gas is a naturally occurring hydrocarbon gas mixture that may be combusted to provide energy or used as a chemical feedstock in the manufacture of plastics and other organic chemicals. Virgin natural gas (e.g., untreated natural gas), as it emerges from natural geologic reservoirs, contains varying amounts of sour gases, particularly carbon dioxide and hydrogen sulfide, also referred to as acid gases. Carbon dioxide reduces the calorific value of the natural gas and hydrogen sulfide may transform into sulfur dioxide, sulfur trioxide, and/or sulfuric acid. An amine gas treating process has been developed to remove these sour gas components from virgin natural gas, thus converting the virgin natural gas into sweet gas (e.g., treated natural gas) that is suitable for combustion in domestic and industrial applications. Unfortunately, large amounts of energy may be expended in pressurizing the amine solutions used in the amine gas treating process, which is then lost (e.g., not recovered) when the sour gases are stripped from the amine solutions.

BRIEF DESCRIPTION OF THE DRAWINGS

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed in detail below, the disclosed embodiments relate generally to natural gas processing, and particularly to an amine gas processing system that processes natural gas using water-based amine solutions (e.g., an alkylamine or amine) and an isobaric pressure exchanger (IPX). For example, the amine gas processing system may include a contactor that removes an acid gas from an untreated natural gas (e.g., virgin natural gas) using an amine in a lean amine stream, thereby generating treated natural gas (e.g., sweet gas) and a rich amine stream. The treated natural gas may be combusted to provide energy or used as a chemical feedstock. The amine gas processing system may also include a regenerator that regenerates the amine in the rich amine stream, thereby generating the lean amine stream and the acid gas. The carbon dioxide and hydrogen sulfide present in the acid gas may be used as feedstocks for other processes, such as a Claus process to produce elemental sulfur or a carbon capture and storage process. The amine gas processing system may also include an IPX that transfers the rich amine stream from the contactor to the regenerator and transfers the lean amine stream from the regenerator to the contactor. Isobaric may be defined as same pressure or constant pressure. Thus, the IPX may include chambers wherein the pressures of two volumes of a liquid may equalize, as described in detail below. In some embodiments, the pressures of the two volumes of liquid may not completely equalize. Thus, the IPX may not only operate isobarically, but also substantially isobarically (e.g., wherein the pressures equalize within approximately +/−1, 2, 3, 4, 5, 6, 7, 8, 9, or 10 percent of each other). In certain embodiments, a first pressure of the rich amine stream may be greater than a second pressure of the lean amine stream. For example, the first pressure may be between approximately 6,000 kPa to 8,000 kPa, 6,500 kPa to 7,500 kPa, or 6,750 kPa to 7,250 kPa greater than the second pressure. Thus, the IPX may be used to transfer pressure from the rich amine stream to the lean amine stream.

Use of such embodiments of the amine gas processing system that include the IPX may provide several advantages compared to other amine gas processing systems that lack the IPX. For example, the amount of energy expended in pressurizing the rich amine stream in the disclosed embodiments may be significantly reduced by using the IPX, thereby reducing the carbon footprint of the amine gas processing system while simultaneously reducing the operating cost through a reduction in electrical power consumption. In addition, as discussed in detail below, certain embodiments of the amine gas processing system may provide the plant operator with control over the extent of mixing between the rich and lean amine streams, thereby assisting the plant operator with improving the overall process. In amine gas processing systems constructed according to the disclosed embodiments, a reduction of capital cost may be achieved through the reduction in size or number of pumps, variable frequency drives (VFDs), recirculation loops, control valves, related equipment, and so forth. Moreover, in situations where the operating capacity of an existing amine gas processing system is limited by electrical power constraints, such as availability, laddered power costs, rationing, or any combination thereof, implementation of the disclosed embodiments may alleviate the electrical power constraints, thereby enabling increased throughput and profitability. Further, the disclosed embodiments may help increase the throughput and profitability of the amine gas processing system by increasing the flow rate of the lean amine stream to the contactor. In addition, use of the disclosed embodiments may reduce the costs associated with expanding the capacity of an existing amine gas processing system, such as by adding an additional processing train or contactor.

Figure 1:
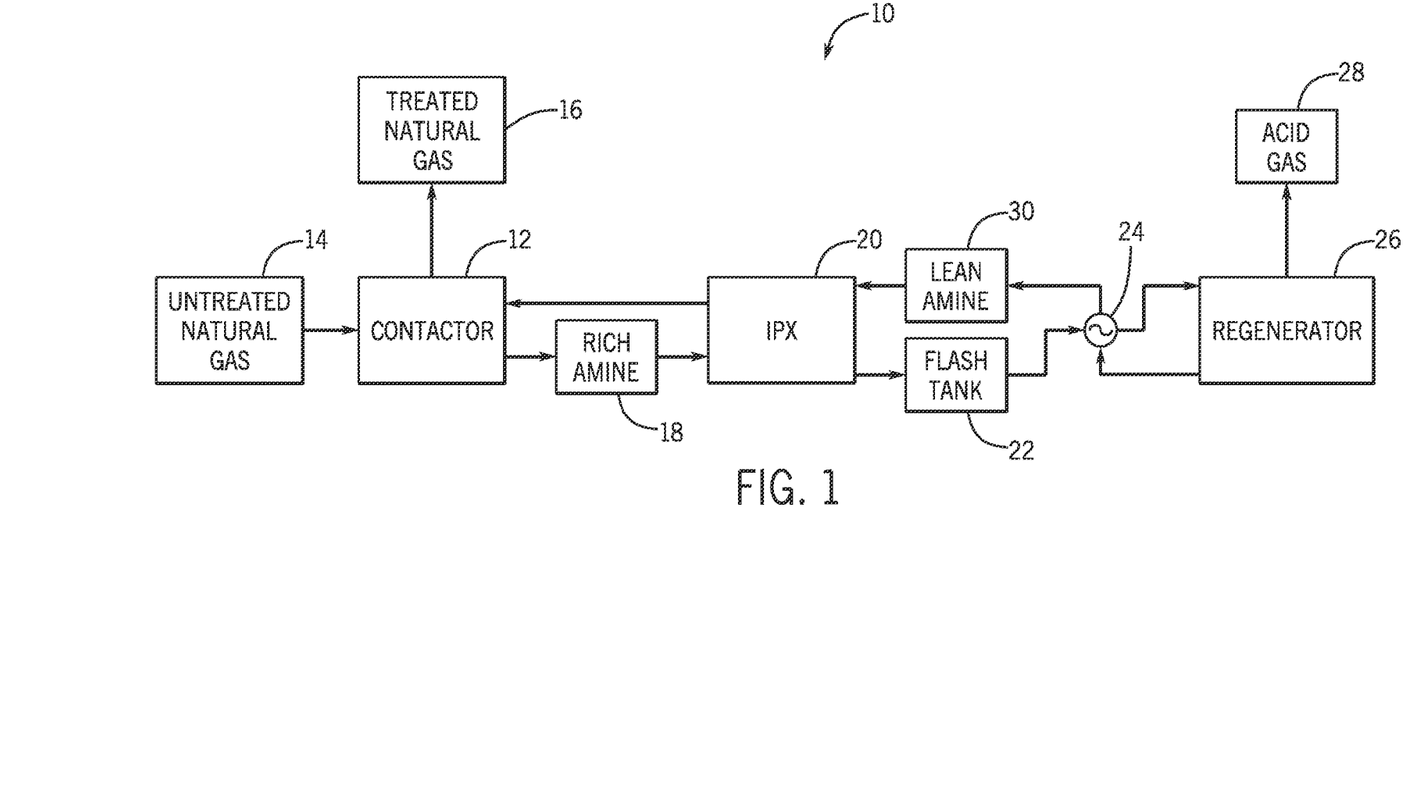
FIG. 1 is a schematic diagram of an embodiment of an amine gas processing system using an isobaric pressure exchanger (IPX)

FIG. 1 is a schematic diagram of an embodiment of an amine gas processing system 10 that may be used for natural gas processing. As shown in FIG. 1, a contactor 12 receives an untreated natural gas 14 (e.g., virgin natural gas), for example, at the bottom of the contactor 12. A lean amine stream 30 (e.g., a liquid) may be fed to the top of the contactor 12. As the untreated natural gas 14 moves upwards in the contactor 12, the natural gas 14 makes intimate contact with the down-flowing lean amine 30. As a result of this interaction within the contactor 12, the sour gases (e.g., acid gases) in the untreated natural gas 14 leave the gas phase stream and enter the liquid phase amine solution stream. Thus, a treated natural gas 16 (e.g., sweet gas) substantially free of the sour gases may leave through the top of the contactor 12.

The untreated natural gas 14 may enter the contactor 12 at pressures up to approximately 8,270 kPa and at a temperature of approximately 30 degrees Celsius. Throughout the following discussion, the term "high-pressure" may refer to pressures associated with operation of the contactor 12 (e.g., up to approximately 6,895 kPa, 7,585 kPa, or 8,270 kPa). The lean amine 30 may enter the contactor 12 at temperatures approximately 3 to 20 degrees Celsius, 4 to 15 degrees Celsius, or 5 to 12 degrees Celsius greater than the inlet temperature of the untreated natural gas 14 to help reduce or prevent condensation of heavier hydrocarbons from the untreated natural gas 14. Because of the exothermicity of the sour gas absorption reactions, the amine solution heats up within the contactor 12 and a rich amine stream 18, laden with sour gas, may leave the bottom of the contactor 12 at temperatures approaching approximately 60 degrees Celsius. The exiting rich amine stream 18 then enters an IPX 20, which reduces the pressure of the rich amine stream 18 to between approximately 475 kPa to 730 kPa, 500 kPa to 715 kPa, or 515 kPa to 690 kPa. The low-pressure rich amine stream 18 is then routed by the IPX 20 through a flash tank 22, where any hydrocarbon gases are allowed to flash off and be recovered, and then to a rich/lean heat exchanger 24 and onwards to a regenerator 26, where the sour gases are stripped from the rich amine 18 through the application of heat. Thus, the rich/lean heat exchanger 24 is used to transfer heat from the lean amine 30 leaving the regenerator 26 to the rich amine 18 entering the regenerator 26. Acid gases 28 (e.g., sour gases) leave the top of the regenerator 26 after being released from the amine solution stream as a result of heating in the regenerator 26. The lean amine 30 coming from the regenerator 26 at pressures between approximately 475 kPa to 730 kPa, 500 kPa to 715 kPa, or 515 kPa to 690 kPa passes through the rich/lean heat exchanger 24 and enters the IPX 20, wherein the pressure of the lean amine stream 30 is increased to the contactor pressure of up to approximately 8,270 kPa. Throughout the following discussion, the term "low-pressure" may refer to pressures associated with operation of the regenerator 26 (e.g., between approximately 475 kPa to 730 kPa, 500 kPa to 715 kPa, or 515 kPa to 690 kPa).

As used herein, the isobaric pressure exchanger (IPX) 20 may be generally defined as a device that transfers fluid pressure between a high-pressure inlet stream (e.g., the rich amine 18 from the contactor 12) and a low-pressure inlet stream (e.g., the lean amine 30 from the regenerator 26) at efficiencies in excess of approximately 50%, 60%, 70%, or 80% without utilizing centrifugal technology. In this context, high pressure refers to pressures greater than the low pressure. The low-pressure inlet stream of the IPX 20 may be pressurized and exit the IPX 20 at high pressure (e.g., at a pressure greater than that of the low-pressure inlet stream), and the high-pressure inlet stream may be depressurized and exit the IPX at low pressure (e.g., at a pressure less than that of the high-pressure inlet stream). Additionally, the IPX 20 may operate with the high-pressure fluid directly applying a force to pressurize the low-pressure fluid, with or without a fluid separator between the fluids. Examples of fluid separators that may be used with the IPX 20 include, but are not limited to, pistons, bladders, diaphragms and the like. In certain embodiments, isobaric pressure exchangers may be rotary or non-rotary devices. Rotary isobaric pressure exchangers (IPXs) 20, such as those manufactured by Energy Recovery, Inc. of San Leandro, Calif., may not have any separate valves, since the effective valving action is accomplished internal to the device via the relative motion of a rotor with respect to end covers, as described in detail below with respect to FIGS. 2-6. Non-rotary IPXs 20 may include separate valves that govern the flow of the high-pressure and low-pressure fluid streams into and out of the device. Both rotary and non-rotary IPXs 20 may be designed to operate with internal pistons to isolate fluids and transfer pressure with little mixing of the inlet fluid streams. Non-rotary IPXs 20 may also be designed with bladders and/or diaphragms, which may provide the same functionality as internal pistons (e.g., isolating fluids and transferring pressure). Reciprocating IPXs 20 may include a piston moving back and forth in a cylinder for transferring pressure between the fluid streams. Any IPX 20 or plurality of IPXs 20 may be used in the disclosed embodiments, such as, but not limited to, rotary IPXs, non-rotary IPXs, reciprocating IPXs, bladder-based IPXs, or any combination thereof. While the discussion with respect to certain embodiments may refer to rotary IPXs 20, it is understood that any IPX 20 or plurality of IPXs 20 may be substituted for the rotary IPX 20 in any of the disclosed embodiments. In addition, the IPX 20 may be disposed on a skid separate from the other components of the amine gas processing system 10, which may be desirable in situations in which the IPX 20 is added to an existing system 10.

Figure 2:
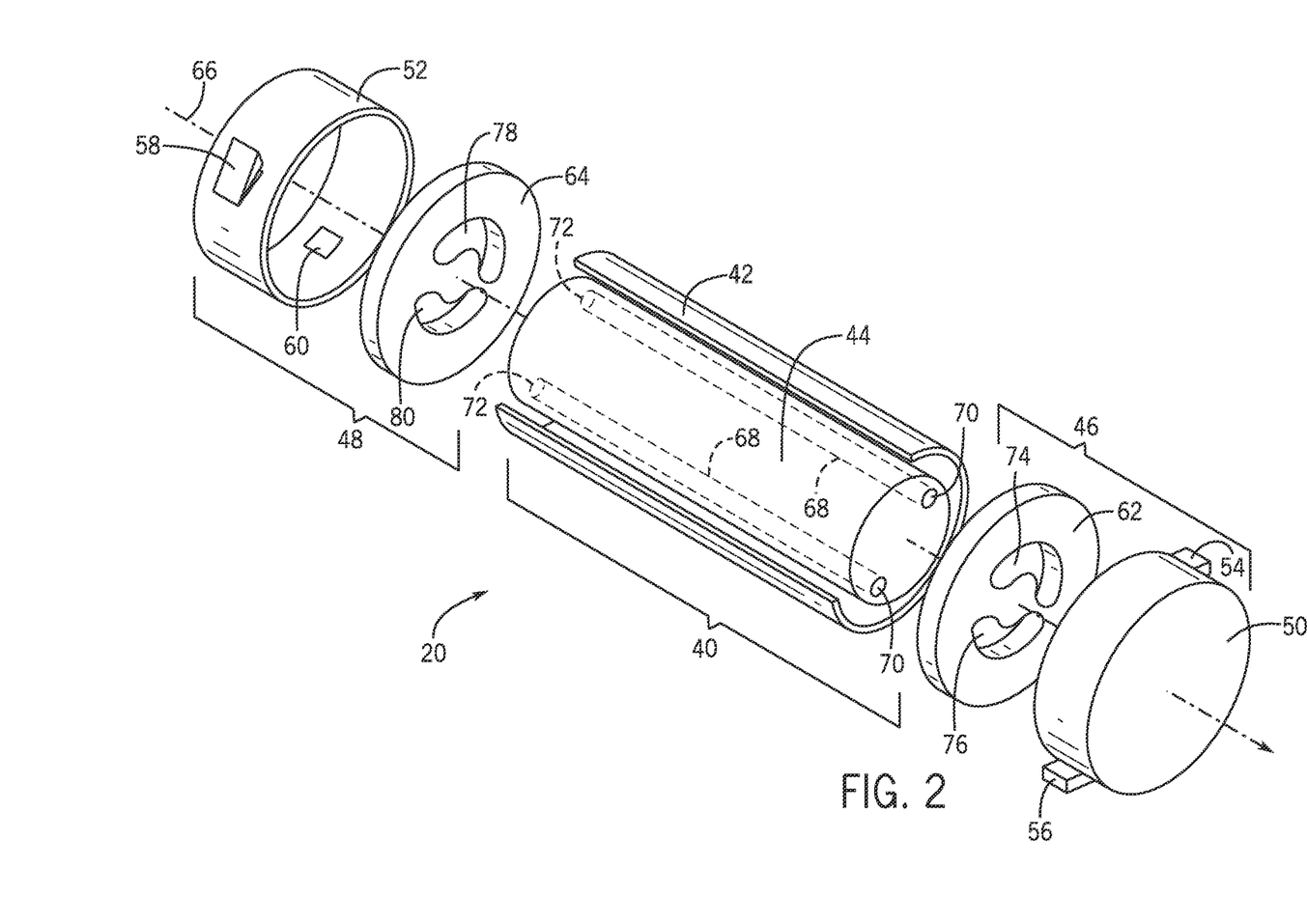
FIG. 2 is an exploded perspective view of an embodiment of a rotary IPX.

FIG. 2 is an exploded view of an embodiment of a rotary IPX 20. In the illustrated embodiment, the rotary IPX 20 may include a generally cylindrical body portion 40 that includes a housing 42 and a rotor 44. The rotary IPX 20 may also include two end structures 46 and 48 that include manifolds 50 and 52, respectively. Manifold 50 includes inlet and outlet ports 54 and 56 and manifold 52 includes inlet and outlet ports 60 and 58. For example, inlet port 54 may receive the high-pressure rich amine stream 18 from the contactor 12 and the outlet port 56 may be used to route the low-pressure rich amine stream 18 to the regenerator 26. Similarly, inlet port 60 may receive the low-pressure lean amine stream 30 from the regenerator 26 and the outlet port 58 may be used to route the high-pressure lean amine stream 30 to the contactor 12. The end structures 46 and 48 include generally flat end plates 62 and 64, respectively, disposed within the manifolds 50 and 52, respectively, and adapted for liquid sealing contact with the rotor 44. The rotor 44 may be cylindrical and disposed in the housing 42, and is arranged for rotation about a longitudinal axis 66 of the rotor 44. The rotor 44 may have a plurality of channels 68 extending substantially longitudinally through the rotor 44 with openings 70 and 72 at each end arranged symmetrically about the longitudinal axis 66. The openings 70 and 72 of the rotor 44 are arranged for hydraulic communication with the end plates 62 and 64, and inlet and outlet apertures 74 and 76, and 78 and 80, in such a manner that during rotation they alternately hydraulically expose liquid at high pressure and liquid at low pressure to the respective manifolds 50 and 52. The inlet and outlet ports 54, 56, 58, and 60, of the manifolds 50 and 52 form at least one pair of ports for high-pressure liquid in one end element 46 or 48, and at least one pair of ports for low-pressure liquid in the opposite end element, 48 or 46. The end plates 62 and 64, and inlet and outlet apertures 74 and 76, and 78 and 80 are designed with perpendicular flow cross sections in the form of arcs or segments of a circle.

With respect to the IPX 20, the plant operator has control over the extent of mixing between the rich and lean amine streams 18 and 30, which may be used to improve the operability of the amine gas processing system 10. For example, varying the proportions of the rich and lean amine streams 18 and 30 entering the IPX 20 allows the plant operator to control the amount of fluid mixing within the system 10. The three characteristics of the IPX 20 that affect mixing are: the aspect ratio of the rotor channels 68, the short duration of exposure between the rich and lean amine streams 18 and 30, and the creation of a liquid barrier (e.g., an interface) between the rich and lean amine streams 18 and 30 within the rotor channels 68. First, the rotor channels 68 are generally long and narrow, which stabilizes the flow within the IPX 20. In addition, the amine streams 18 and 30 may move through the channels 68 in a plug flow regime with very little axial mixing. Second, in certain embodiments, at a rotor speed of approximately 1200 RPM, the time of contact between the rich and lean amine streams 18 and 30 may be less than approximately 0.15 seconds, 0.10 seconds, or 0.05 seconds, which again limits mixing of the streams 18 and 30. Third, a small portion of the rotor channel 68 is used for the exchange of pressure between the streams 18 and 30. Therefore, a volume of amine remains in the channel 68 as a barrier between the rich and lean amine streams 18 and 30. All these mechanisms may limit mixing within the IPX 20.

In addition, because the IPX 20 is configured to be exposed to the rich amine stream 18 and the lean amine stream 30, certain components of the IPX 20 may be made from materials compatible with the components of the streams 18 and 30. For example, in certain embodiments, the housing 42 may be made from a duplex stainless steel. Other components of the IPX 20 may also be made from materials suitable for use with the rich and lean amine streams 18 and 30. In addition, certain components of the IPX 20 may be configured to be physically compatible with other components of the amine gas processing system 10. For example, the ports 54, 56, 58, and 60 may comprise flanged connectors to be compatible with other flanged connectors present in the piping of the amine gas processing system 10. In other embodiments, the ports 54, 56, 58, and 60 may comprise threaded or other types of connectors.

FIGS. 3-6 are exploded views of an embodiment of the rotary IPX 20 illustrating the sequence of positions of a single channel 68 in the rotor 44 as the channel 68 rotates through a complete cycle, and are useful to an understanding of the rotary IPX 20. It is noted that FIGS. 3-6 are simplifications of the rotary IPX 20 showing one channel 68 and the channel 68 is shown as having a circular cross-sectional shape. In other embodiments, the rotary IPX 20 may include a plurality of channels 68 with different cross-sectional shapes. Thus, FIGS. 3-6 are simplifications for purposes of illustration, and other embodiments of the rotary IPX 20 may have configurations different from that shown in FIGS. 3-6. As described in detail below, the rotary IPX 20 facilitates a hydraulic exchange of pressure between two liquids by putting them in momentary contact within a rotating chamber. In certain embodiments, this exchange happens at a high speed that results in very high efficiency with very little mixing of the liquids.

Figures 3, 4, 5, 6:
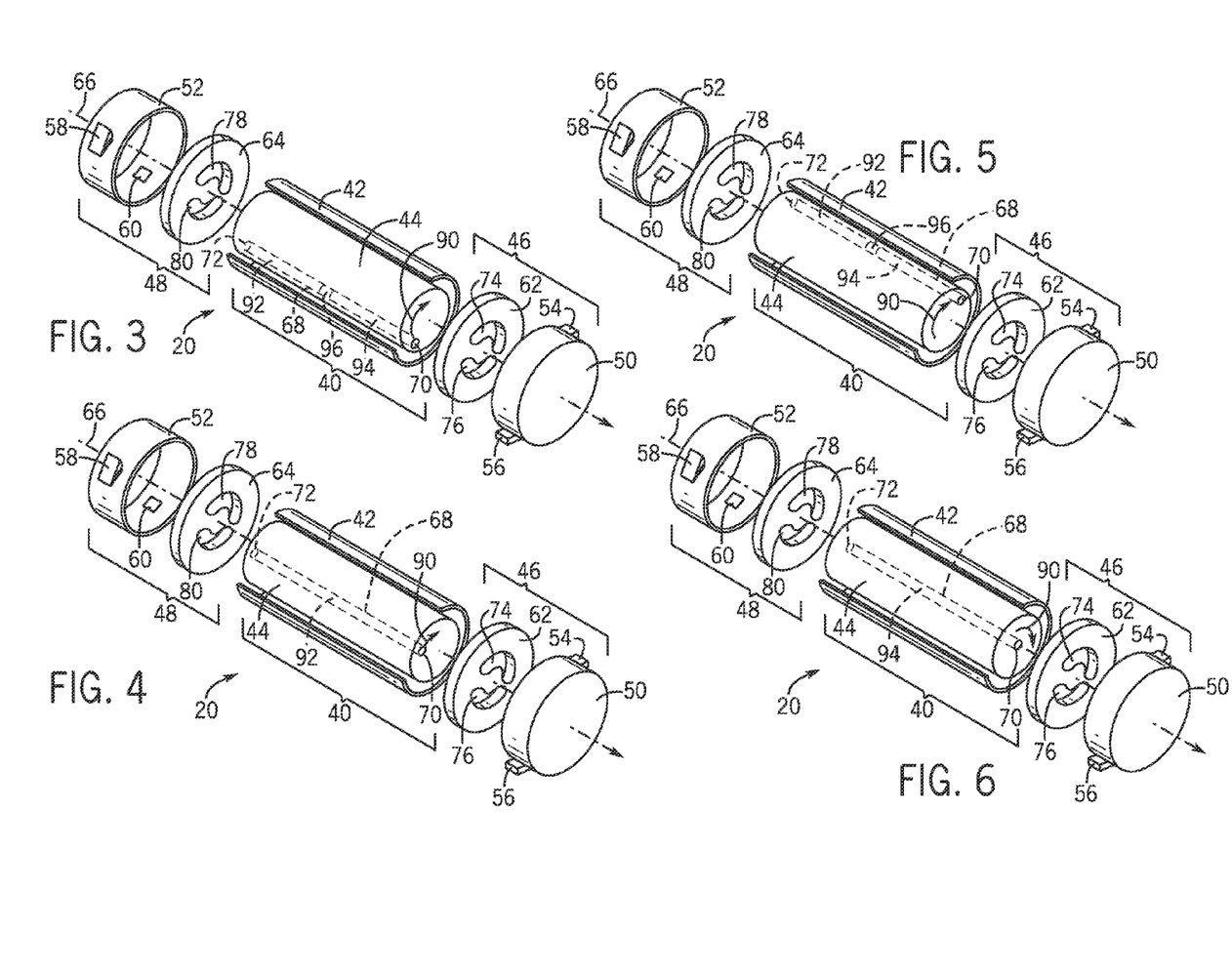
FIG. 3 is an exploded perspective view of an embodiment of a rotary IPX in a first operating position.
FIG. 4 is an exploded perspective view of an embodiment of a rotary IPX in a second operating position.
FIG. 5 is an exploded perspective view of an embodiment of a rotary IPX in a third operating position.
FIG. 6 is an exploded perspective view of an embodiment of a rotary IPX in a fourth operating position.

In FIG. 3, the channel opening 70 is in hydraulic communication with aperture 76 in endplate 62 and therefore with the manifold 50 at a first rotational position of the rotor 44 and opposite channel opening 72 is in hydraulic communication with the aperture 80 in endplate 64, and thus, in hydraulic communication with manifold 52. As discussed below, the rotor 44 rotates in the clockwise direction indicated by arrow 90. As shown in FIG. 3, low-pressure lean amine 92 (e.g., lean amine 30 from the regenerator 26) passes through end plate 64 and enters the channel 68, where it pushes rich amine 94 (e.g., rich amine 18 from the contactor 12) out of the channel 68 and through end plate 62, thus exiting the rotary IPX 20. The lean amine 92 and rich amine 94 contact one another at an interface 96 where minimal mixing of the liquids occurs because of the short duration of contact. The interface 96 is a direct contact interface because the lean amine 92 directly contacts the rich amine 92.

In FIG. 4, the channel 68 has rotated clockwise through an arc of approximately 90 degrees, and outlet 72 is now blocked off between apertures 78 and 80 of end plate 64, and outlet 70 of the channel 68 is located between the apertures 74 and 76 of end plate 62 and, thus, blocked off from hydraulic communication with the manifold 50 of end structure 46. Thus, the low-pressure lean amine 92 is contained within the channel 68.

In FIG. 5, the channel 68 has rotated through approximately 180 degrees of arc from the position shown in FIG. 3. Opening 72 is in hydraulic communication with aperture 78 in end plate 64 and in hydraulic communication with manifold 52, and the opening 70 of the channel 68 is in hydraulic communication with aperture 74 of end plate 62 and with manifold 50 of end structure 46. The liquid in channel 68, which was at the pressure of manifold 52 of end structure 48, transfers this pressure to end structure 46 through outlet 70 and aperture 74, and comes to the pressure of manifold 50 of end structure 46. Thus, high-pressure rich amine 94 (e.g., rich amine 18 from the contactor 12) pressurizes and displaces the lean amine 92.

In FIG. 6, the channel 68 has rotated through approximately 270 degrees of arc from the position shown in FIG. 3, and the openings 70 and 72 of channel 68 are between apertures 74 and 76 of end plate 62, and between apertures 78 and 80 of end plate 64. Thus, the high-pressure rich amine 94 is contained within the channel 68. When the channel 68 rotates through approximately 360 degrees of arc from the position shown in FIG. 3, the lean amine 92 displaces the rich amine 94, restarting the cycle.

Figure 7:
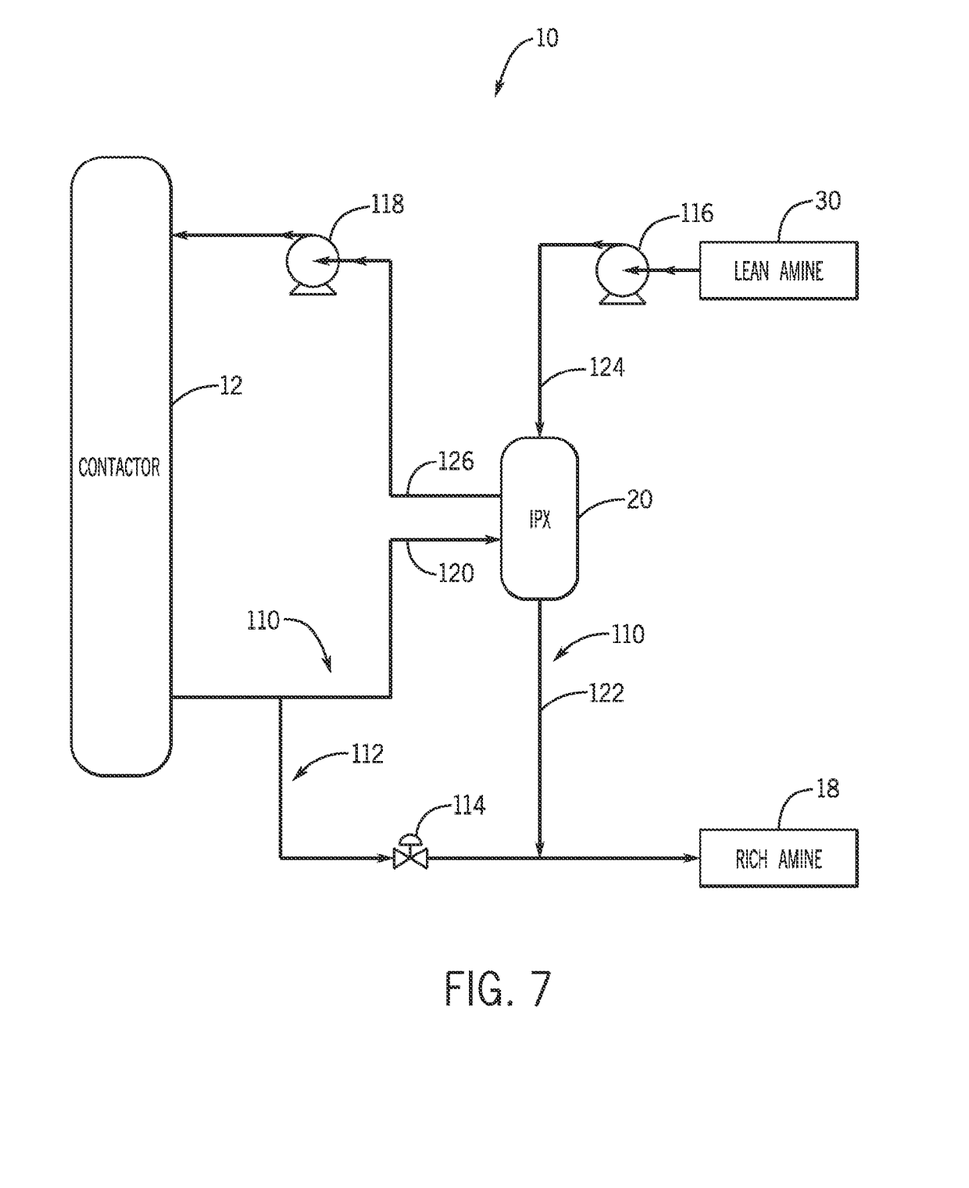
FIG. 7 is a diagram of an embodiment of an amine gas processing system with an IPX in parallel with a control valve.

FIG. 7 is a diagram of an embodiment of the amine gas processing system 10 with the IPX 20 in parallel with a control valve 114. Specifically, the IPX 20 may be disposed in a normal loop 110 that routes the rich amine 18 from the contactor 12 to the regenerator 26, as described in detail below. In addition, a bypass loop 112 may include a flow control valve 114 for routing the rich amine 18 from the contactor 12 to the regenerator 26 without passing through the IPX 20. Thus, once the high-pressure rich amine 18 leaves the contactor 12, the full flow does not go to the IPX 20. Instead, a portion of the flow of rich amine 18 enters the IPX 20 and the remainder of the flow goes through the flow control valve 114. The flows of rich amine 18 are recombined upstream of the flash tank 22, thus maintaining approximately constant pressure (e.g., within approximately +/−1, 2, 3, 4, 5, 6, 7, 8, 9, or 10% of each other) and flow in the system. In certain embodiments, the flow control valve 114 may serve as a level control valve for the contactor 12 by maintaining a desired amine solution liquid level in the bottom of the contactor 12 to help prevent any gas from exiting the contactor 12 through the bottom end liquid phase piping. In addition, the flow control valve 114 may be used by the plant operator to vary the amount of rich amine 18 entering the IPX 20. Although use of the flow control valve 114 may lower the overall efficiency of the system 10 as a portion of the pressure energy is lost at the flow control valve 114, it allows the plant operator to have finer control over the system 10 by using the flow control valve 114 to maintain level control of the contactor 12 to avoid gas from exiting the bottom of the contactor 12, for example. As with the IPX 20, the flow control valve 114 may reduce the pressure of the rich amine stream 18 to between approximately 475 kPa to 730 kPa, 500 kPa to 715 kPa, or 515 kPa to 690 kPa. However, in contrast to the IPX 20, pressure energy that is relieved in the flow control valve 114 is essentially wasted. In other words, the IPX 20 uses the pressure energy from reducing the pressure of the rich amine 18 to increase the pressure of the lean amine entering the contactor 12. Thus, it may be desirable to reduce or eliminate use of the flow control valve 114 to improve the overall efficiency of amine gas processing system 10. In other embodiments, the IPX 20 may completely replace the flow control valve 114, which is then omitted, thereby eliminating the waste of pressure energy by the flow control valve 114. In further embodiments, the flow control valve 114 may be present, but normally remains closed. Thus, although the flow control valve 114 may not normally be used, the valve 114 may be opened when desired. By using the IPX 20 to either eliminate or reduce use of the flow control valve 114, the amine gas processing system 10 may use much less energy to pressurize the lean amine 30 entering the contactor 12 compared to systems that do not include the IPX 20.

As shown in FIG. 7, in certain embodiments, there are four fluid connections to the IPX 20, namely a rich amine inlet 120 (high pressure), a rich amine outlet 122 (low pressure), a lean amine inlet 124 (low pressure), and a lean amine outlet 126 (high pressure). As described above, the lean amine 30 enters the IPX 20 at low pressure and is pressurized by the incoming high-pressure rich amine 18 coming from the bottom of the contactor 12 at a pressure approximately equal to that of the contactor 12 (e.g., up to approximately 6,895 kPa, 7,585 kPa, or 8,270 kPa). The lean amine 30 leaves the IPX 20 at high pressure and may pass through a circulation pump 118 before entering the top of the contactor 12. The circulation pump 118 may be used to pressurize the lean amine 30 to a pressure substantially equal to that of the contactor 12 and may be used to overcome an inefficiency of the IPX 20 and/or pressure losses in lines between the regenerator 26 and the contactor 12. The rich amine 18 leaves the IPX 20 at low pressure (e.g., between approximately 475 kPa to 730 kPa, 500 kPa to 715 kPa, or 515 kPa to 690 kPa) and is sent to the flash tank 22 and regenerator 26. Low-pressure lean amine 30 leaves the regenerator 26 at low pressure and enters the IPX 20, thereby restarting the cycle. In certain embodiments, one or more pumps 116 may be used to pressurize the lean amine 30 before reaching the IPX 20. For example, because of certain process conditions, a low-pressure feed pump 116 may be added to the amine gas processing system 10 prior to the lean amine 30 entering the IPX 20. In further embodiments, the amine gas processing system 10 may include none, one, or both of the pumps 116 and 118.

Figure 8:
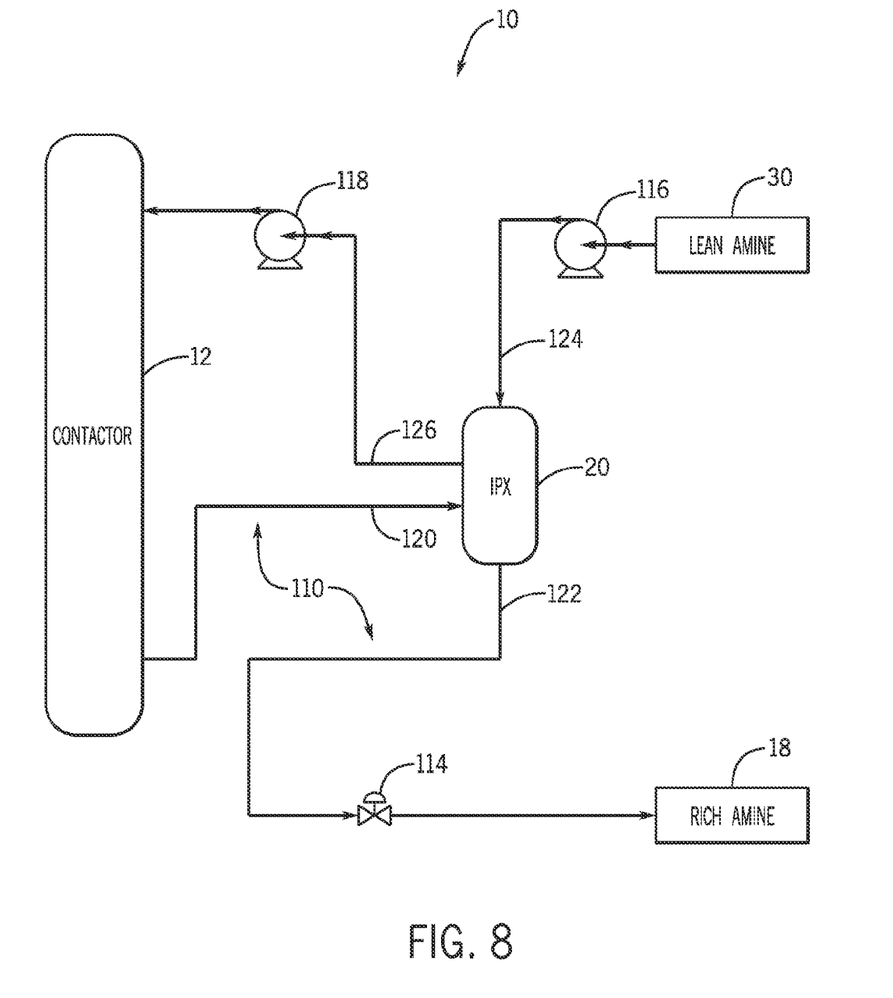
FIG. 8 is a diagram of an embodiment of an amine gas processing system with an IPX in series with a control valve.

FIG. 8 is a diagram of an embodiment of the amine gas processing system 10 with the IPX 20 in series with the flow control valve 114. In the illustrated embodiment, the rich amine 18 exits the IPX 20 from the rich amine outlet 122 and enters the flow control valve 114, which allows the flow control valve 114 to regulate the flow of the rich amine 18 to the flash tank 22, as well as adjust the backpressure within the IPX 20. For example, closing the flow control valve 114 may increase the backpressure within the IPX 20 and opening the flow control valve 114 may decrease the backpressure within the IPX 20. The illustrated embodiment allows for the entire flow of high-pressure rich amine 18 leaving the contactor 12 to pass through the IPX 20, while still maintaining flow control to the flash tank 22 and level control to the contactor 12 via use of the flow control valve 114. In other respects, the illustrated embodiment is similar to that shown in FIG. 7.

Figure 9:
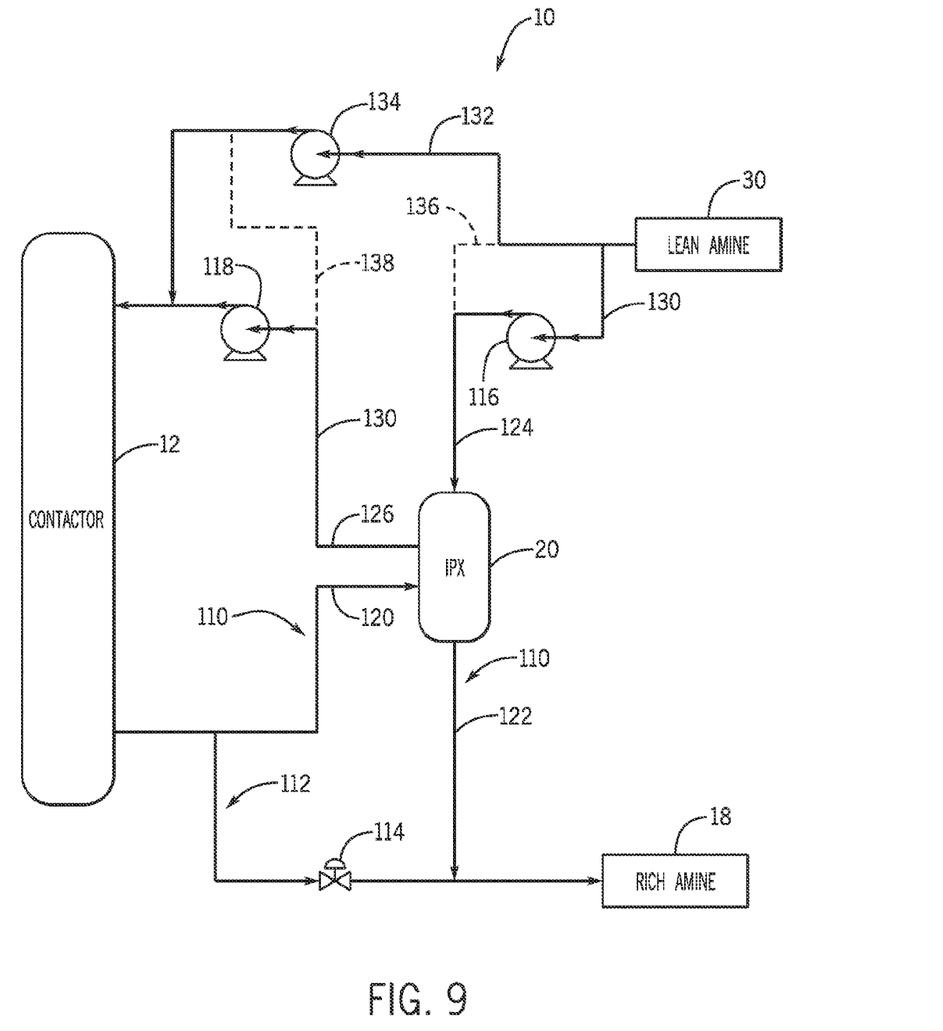
FIG. 9 is a diagram of an embodiment of an amine gas processing system with an IPX and a high-pressure pump.

FIG. 9 is a diagram of an embodiment of the amine gas processing system 10 with the IPX 20 and an additional pump for the lean amine 30. Specifically, the IPX 20 may be disposed in a normal loop 130 that routes the lean amine 30 from the regenerator 26 to the contactor 12, as described in detail below. In addition, a bypass loop 132 may include a high-pressure pump 134 for routing the lean amine 30 from the regenerator 26 to the contactor 12 without passing through the IPX 20. In other words, the low-pressure lean amine 30 from the regenerator 26 splits off into two separate flows, the normal and bypass loops 130 and 132. The normal loop 130 runs to the low-pressure lean amine inlet 124 of the IPX 20, where the lean amine 30 is pressurized by the high-pressure rich amine stream 18 from the bottom of the contactor 12 and leaves the IPX 20 at high pressure. From there the lean amine 30 may receive a slight pressure increase from the circulation pump 118 before reaching the pressure of the contactor 12. Because of certain process conditions, the amine gas processing system 10 may also include the low-pressure feed pump 116.

The bypass loop 132 shown in FIG. 9 includes a high-pressure pump 134 where the lean amine 30 is brought to the pressure of the contactor 12 before recombining with the flow from the IPX 20 and entering the top of the contactor 12. Use of the high-pressure pump 134 with the IPX 20 may allow for a higher flow rate of the lean amine 30 to the contactor 12 than either the IPX 20 or the high-pressure pump 134 could provide separately. The illustrated embodiment would also allow the plant operator to independently control the flow in each loop 130 and 132, allowing the plant operator to adjust the amount of mixing of rich amine 18 with lean amine 30 that occurs in the IPX 20, so that the lean amine 30 entering the contactor 12 meets plant specifications. For example, one way to reduce mixing in the IPX 20 is to supply excess lean amine 30 to clear the channels 68 of any residual rich amine fluid 18, which may be referred to as overflush. Overflush may reduce mixing in the IPX 20 depending on the amount of overflush. Zero overflush may be referred to as "balanced flow" when the inlet flow rate of the lean amine 30 to the IPX 20 substantially equals the outlet flow rate of the lean amine 30. The amount of overflush may either be set manually using independent controller systems for both pumps 116 and 118, or automatically set using a flow balancing function using linked or slaved VFDs.

In certain embodiments, the piping connections for the high-pressure pump 134 may be different than that described above. For example, the lean amine 30 flowing from the regenerator 26 to the IPX 20 may pass through an inlet pipe 136, thereby bypassing the low-pressure feed pump 116. Thus, the inlet pipe 136 may be used when the low-pressure feed pump 116 is not in service or when the additional pressure increase provided by the pump 116 is not desired. Additionally or alternatively, the lean amine 30 from the high-pressure pump 134 may pass through an outlet pipe 138 and enter the circulation pump 118 instead of entering the contactor 12 directly at the outlet side of the pump 118. Thus, the outlet pipe 138 may be used when the additional pressure increase provided by the circulation pump 118 is desired.

In other embodiments, the piping arrangement with respect to pumps 116, 118, and 134, and the IPX 20 may be different from than shown in FIG. 9. For example, the high-pressure pump 134 may be used in place of the low-pressure feed pump 116. In other words, low-pressure lean amine 30 from the regenerator 26 may flow through the high-pressure pump 134 before reaching the IPX 20. In such embodiments, the motor of the high-pressure pump 134 may be driven much slower than normal, as the pump 134 is being used to provide a slight pressure increase to the lean amine 30 prior to entering the IPX 20. The majority of the pressure increase in the lean amine 30 will come from the pressure transferred from the rich amine 18 entering the IPX 20 from the bottom of the contactor 12. Use of the high-pressure pump 134 in this manner may provide a significant energy savings as the pump 134 provides a small pressure rise rather than increasing the lean amine 30 to the full pressure of the contactor 12. In addition, this embodiment gives the plant operator the option of running the high-pressure pump 134 much slower than the plant operator would without the IPX 20, run fewer pumps at once (if in a multiple pump arrangement), or use a smaller pump without affecting the amount of high-pressure lean amine 30 entering the contactor 12. In other respects, the illustrated embodiment of FIG. 9 is similar to those shown in the previous figures.

Figure 10:
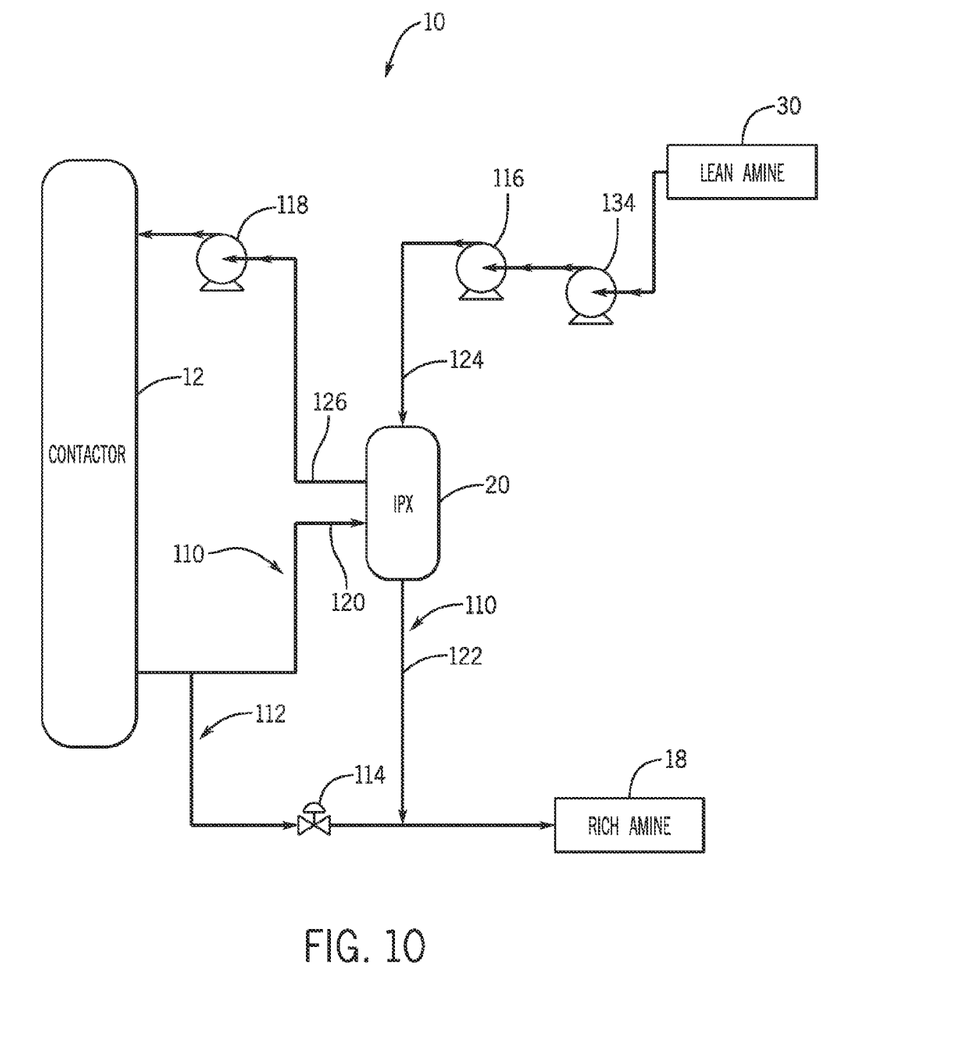
FIG. 10 is a diagram of an embodiment of an amine gas processing system with an IPX and a high-pressure pump in series with a low-pressure pump.

FIG. 10 is a diagram of an embodiment of the amine gas processing system 10 with the IPX 20 and the high-pressure pump 134 in series with the low-pressure pump 116. This embodiment allows the plant operator to have the option to run either pump 134 or 116 separately or run both pumps 134 and 116 simultaneously to tailor the low-pressure lean amine 30 flow rate and/or pressure in response to particular situations faced by the plant operator. For example, in certain situations, use of both pumps 134 and 116 may provide a higher flow rate of the lean amine 30 to the contactor 12 than use of either pump 134 or 116 alone. Although the high-pressure pump 134 is shown upstream of the low-pressure feed pump 116 in FIG. 10, in other embodiments, the low-pressure feed pump 116 may be upstream of the high-pressure pump 134. In other respects, the illustrated embodiment of FIG. 10 is similar to those shown in the previous figures.

Figure 11:
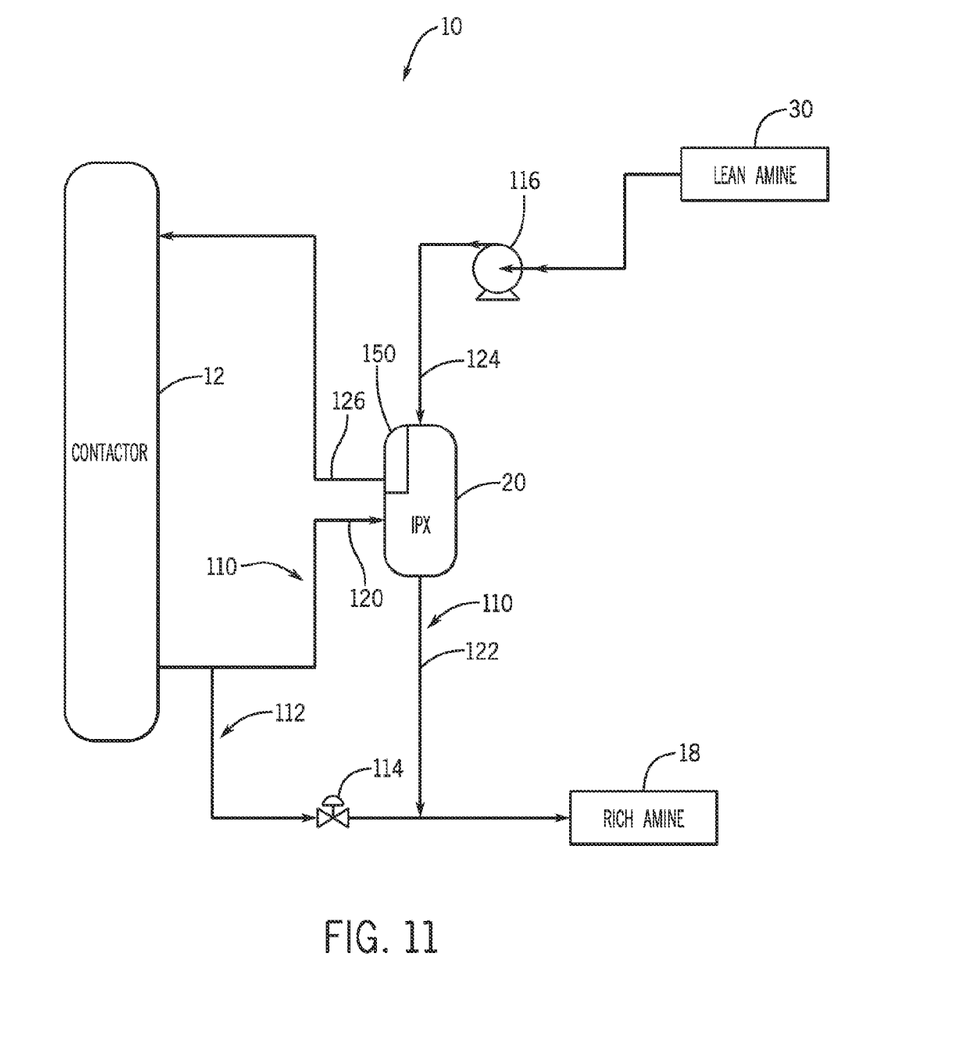
FIG. 11 is a diagram of an embodiment of an amine gas processing system with an IPX having an integrated high-pressure pump.

FIG. 11 is a diagram of an embodiment of the amine gas processing system 10 with the IPX 20 having an integrated high-pressure pump 150. Specifically, the integrated high-pressure pump 150 may be contained within the IPX 20 itself. In this embodiment, the IPX 20 is permanently coupled to the integrated high-pressure pump 150 within the housing of the IPX 20. The integrated high-pressure pump 150 may be externally powered and controlled by the software for the amine gas processing system 10. The high-pressure lean amine 30 coming out of the chambers of the IPX 20 passes through the integrated high-pressure pump 150 and exits the IPX 20 at approximately the full pressure of the contactor 12. This embodiment allows for the amine gas processing system 10 to operate without an external circulation pump, such as circulation pump 118, thereby leading to a smaller physical system footprint as well as potential equipment cost savings. In other embodiments, one or more of the pumps 116, 118, or 134 may be integrated with the IPX 20 in manner similar to that of the integrated high-pressure pump 150. In other respects, the illustrated embodiment of FIG. 11 is similar to those shown in the previous figures.

As described above, certain embodiments of the amine gas processing system 10 may include the contactor 12 to remove the acid gas 28 from the untreated natural gas 14 using an amine in the lean amine stream 30, thereby generating the treated natural gas 16 and the rich amine stream 18. The system 10 may also include the regenerator 26 to regenerate the amine in the rich amine stream 18, thereby generating the lean amine stream 30 and the acid gas 28. The system 10 may also include the IPX 20 to transfer the rich amine stream 18 from the contactor 12 to the regenerator 26 and to transfer the lean amine 30 from the regenerator 26 to the contactor 12. The IPX 20 may also transfer pressure from the rich amine stream 18 entering the IPX 20 to the lean amine stream 30 leaving the IPX 20. Thus, use of the IPX 20 may reduce the amount of energy expended in pressurizing the amine solution in the system 10, thereby reducing the operating costs of the system 10. In addition, use of the IPX 20 may provide the plant operator with additional flexibility in operating the system 10, reduce capital costs associated with the system 10, increase the operating capacity of the system 10, increase the profitability of the system 10, and/or reduce costs associated with expanding the system 10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system, comprising:
    an amine gas processing system, comprising:
        a contactor configured to remove an acid gas from an untreated natural gas using an amine in a lean amine stream, output a treated natural gas, and output a rich amine stream;
        a regenerator configured to regenerate the amine in the rich amine stream, output the lean amine stream, and output the acid gas; and
        an isobaric pressure exchanger configured to transfer the rich amine stream from the contactor to the regenerator and to transfer the lean amine stream from the regenerator to the contactor, wherein the isobaric pressure exchanger is configured to transfer pressure from the rich amine stream entering the isobaric pressure exchanger at a first pressure to the lean amine stream leaving the isobaric pressure exchanger at a second pressure, wherein the first pressure is greater than the second pressure.

2. The system of claim 1, wherein the isobaric pressure exchanger comprises at least one of a rotary isobaric pressure exchanger, a non-rotary isobaric pressure exchanger, a reciprocating isobaric pressure exchanger, or a bladder-based isobaric pressure exchanger, or any combination thereof.

3. The system of claim 1, wherein an outer housing of the isobaric pressure exchanger comprises duplex stainless steel.

4. The system of claim 1, wherein the isobaric pressure exchanger comprises at least one of flanged connectors, or threaded connectors, or any combination thereof.

5. The system of claim 1, wherein the isobaric pressure exchanger comprises:
    a housing having a body portion;
    first and second ends plates at opposite ends of the body portion, wherein each of the end plates has an inlet aperture and an outlet aperture for respective liquid flow; and
    a rotor disposed in the body portion of the housing, wherein the rotor has ends in substantially sealing contact with the end plates, wherein the rotor has at least one channel therein extending substantially longitudinally from one end of the rotor to an opposite end of the rotor, wherein the channel has an opening in each of the ends of the rotor configured to contain at least one of the rich amine stream, or the lean amine stream, or any combination thereof.

6. The system of claim 1, comprising a flow control valve configured to transfer the rich amine stream from the contactor to the regenerator, wherein the flow control valve is disposed in a rich amine bypass loop around the isobaric pressure exchanger.

7. The system of claim 1, comprising a flow control valve disposed between the isobaric pressure exchanger and the regenerator, wherein the flow control valve is configured to adjust a flow rate of the rich amine stream to the regenerator.

8. The system of claim 1, comprising a first pump configured to transfer the lean amine stream from the regenerator to the isobaric pressure exchanger.

9. The system of claim 8, comprising a second pump configured to transfer the lean amine stream from the regenerator to the first pump.

10. The system of claim 1, comprising a circulation pump configured to transfer the lean amine stream from the isobaric pressure exchanger to the contactor.

11. The system of claim 1, comprising a third pump configured to transfer the lean amine stream from the regenerator to the contactor, wherein the third pump is disposed in a lean amine bypass loop around the isobaric pressure exchanger.

12. The system of claim 1, wherein the isobaric pressure exchanger comprises an integrated fourth pump configured to transfer the lean amine stream from the isobaric pressure exchanger to the contactor.

13. A system, comprising:
    an amine gas processing system, comprising:
        a contactor configured to remove an acid gas from an untreated natural gas using an amine in a lean amine stream, output a treated natural gas, and output a rich amine stream;
        a regenerator configured to regenerate the amine in the rich amine stream, output the lean amine stream, and output the acid gas;
        an isobaric pressure exchanger configured to transfer the rich amine stream from the contactor to the regenerator and to transfer the lean amine stream from the regenerator to the contactor, and the isobaric pressure exchanger is configured to transfer pressure from the rich amine stream entering the isobaric pressure exchanger at a first pressure to the lean amine stream leaving the isobaric pressure exchanger at a second pressure, wherein the first pressure is greater than the second pressure, wherein the isobaric pressure exchanger comprises:
            a housing having a body portion;
            first and second ends plates at opposite ends of the body portion, wherein each of the end plates has an inlet aperture and an outlet aperture for respective liquid flow; and
            a rotor disposed in the body portion of the housing, wherein the rotor has ends in substantially sealing contact with the end plates, wherein the rotor has at least one channel therein extending substantially longitudinally from one end of the rotor to an opposite end of the rotor, wherein the channel has an opening in each of the ends of the rotor configured to contain at least one of the rich amine stream, or the lean amine stream, or any combination thereof;
        a flow control valve configured to transfer the rich amine stream from the contactor to the regenerator, wherein the flow control valve is disposed in a rich amine bypass loop around the isobaric pressure exchanger;

a first pump configured to transfer the lean amine stream from the regenerator to the isobaric pressure exchanger; and a circulation pump configured to transfer the lean amine stream from the isobaric pressure exchanger to the contactor.

* * * * *